United States Patent
Vangara et al.

(10) Patent No.: US 9,566,233 B2
(45) Date of Patent: Feb. 14, 2017

(54) ONDANSETRON SUBLINGUAL SPRAY FORMULATION

(71) Applicant: Insys Pharma, Inc., Chandler, AZ (US)

(72) Inventors: Kiran Kumar Vangara, Phoenix, AZ (US); Chandeshwari Shivani Chilampalli, Phoenix, AZ (US); Venkat R. Goskonda, Phoenix, AZ (US)

(73) Assignee: INSYS DEVELOPMENT COMPANY, INC., Chandler, AZ (US)

( * ) Notice: Subject to any disclaimer, the term of this patent is extended or adjusted under 35 U.S.C. 154(b) by 0 days.

(21) Appl. No.: 14/541,439

(22) Filed: Nov. 14, 2014

(65) Prior Publication Data

US 2015/0133517 A1    May 14, 2015

Related U.S. Application Data

(60) Provisional application No. 61/904,236, filed on Nov. 14, 2013.

(51) Int. Cl.

| | | |
|---|---|---|
| *A61K 31/4178* | (2006.01) | |
| *A61K 47/40* | (2006.01) | |
| *A61K 47/10* | (2006.01) | |
| *A61K 9/00* | (2006.01) | |
| *A61K 31/00* | (2006.01) | |

(52) U.S. Cl.
CPC ............ *A61K 9/006* (2013.01); *A61K 31/00* (2013.01); *A61K 31/4178* (2013.01); *A61K 47/10* (2013.01); *A61K 47/40* (2013.01)

(58) Field of Classification Search
IPC ............ A61K 9/006,31/4178, 47/40, 47/10
See application file for complete search history.

(56) References Cited

U.S. PATENT DOCUMENTS

| | | | |
|---|---|---|---|
| 5,166,145 A | 11/1992 | Jao et al. | |
| 7,022,712 B2 | 4/2006 | Yalkowsky | |
| 2004/0141923 A1 | 7/2004 | Dugger, III et al. | |
| 2005/0002867 A1* | 1/2005 | Dugger et al. | 424/44 |
| 2006/0062812 A1* | 3/2006 | Ross | A61K 9/006 |
| | | | 424/400 |
| 2007/0261695 A1 | 11/2007 | Kottayil et al. | |
| 2008/0171089 A1* | 7/2008 | Blondino et al. | 424/489 |
| 2009/0010992 A1 | 1/2009 | Palmer et al. | |
| 2011/0171140 A1 | 7/2011 | Illum et al. | |
| 2011/0171273 A1 | 7/2011 | Blondino et al. | |
| 2012/0064094 A1 | 3/2012 | Chabbert et al. | |

OTHER PUBLICATIONS

Warr Current Oncology 15(1); S4-S9.*
Cancer.net (2015).*
Drug.com (2015).*
Hospira, Ondansetron Material Safety Datasheet, Global Occupational Toxicity, Nov. 6, 2009, bdipharma.com/MSDS/Hospira/Ondansetron.pdf.
Cubeddu L.X., et al., Antagonism of serotonin S3 receptors with ondansetron prevents nausea and emesis, J Clin Oncol, Oct. 1990, 8(10), 1721-1727. Abstract.
Paventi S., et al., Efficacy of a single-dose ondansetron for preventing post-operative nausea and vomiting after laparoscopic cholecystectomy with sevoflurane and remifentanil infusion anaesthesia, Eur Rev Med Pharmacol Sci, Mar.-Apr. 2001, 5(2), 59-63.
International Search Report for corresponding PCT application No. PCT/US2014/065646 published on Jan. 26, 2015.
Ni N et al., Solubilization and preformulation of carbendazim, Int J Pharm., Sep. 5, 2002, 244(1-2), 99-104.

* cited by examiner

*Primary Examiner* — Shirley V Gembeh
(74) *Attorney, Agent, or Firm* — Wood, Phillips, Katz, Clark & Mortimer

(57) ABSTRACT

The invention is directed to sublingual spray formulations containing ondansetron or a pharmaceutically acceptable salt thereof and water. The invention is further directed to methods for treating or preventing nausea and emesis associated with cancer treatments by administering sublingual spray formulations containing ondansetron or a pharmaceutically acceptable salt thereof to a patient in need thereof.

14 Claims, No Drawings

ONDANSETRON SUBLINGUAL SPRAY FORMULATION

FIELD OF THE INVENTION

The invention is directed to sublingual spray formulations containing ondansetron or a pharmaceutically acceptable salt thereof. The invention is further directed to method for treating or preventing nausea and emesis associated with cancer treatments by administering sublingual spray formulations containing ondansetron or a pharmaceutically acceptable salt thereof to a patient in need thereof.

BACKGROUND OF THE INVENTION

Ondansetron is a serotonin 5-HT3 receptor antagonist with the following structure:

Ondansetron's primary use is as an antiemetic (to treat nausea and vomiting) following cancer treatments such as chemotherapy, surgery and/or radiation. Ondansetron works by reducing the activity of the vagus nerve which then deactivates the vomiting center in the medulla oblongata. Ondansetron also blocks serotonin receptors in the chemoreceptor trigger zone.

Ondansetron is currently available from GlaxoSmithKline as a film coated tablet, an oral solution, as an injection (Zofran®), and an orally disintegrating tablet (Zofran ODT®). Ondansetron is also available as an oral soluble film (Zuplenz®) from Vestiq Pharmaceuticals.

U.S. Pat. No. 6,998,110 discloses a method for administering a composition, such as ondansetron, to a mammal through the oral mucosa. This patent teaches that a polar solvent and a propellant are required. Although U.S. Pat. No. 6,676,931 teaches a propellant free ondansetron composition, this patent requires the use of a pharmacologically acceptable polar solvent in an amount of 19 to 90 weight percent and flavoring agent in an amount of 0.1 to 10 weight percent of the total composition.

U.S. Pat. No. 5,854,270 is directed to a liquid ondansetron formulation that includes a sorbitol-containing sweetener and has a pH of from 2 to 5. U.S. Pat. No. 6,555,546 discloses a formulation which may contain ondansetron and polyethylene glycol (PEG)-electrolyte solution for use in treating constipation or for accelerating intestinal lavage. However, these formulations fail to provide a sublingual formulation that has quick-onset and is storage stable.

"Sublingual" means "under the tongue" and refers to administration of a substance via the mouth in such a way that the substance is rapidly absorbed via the blood vessels under the tongue. A sublingual formulation is desirable because it bypasses hepatic first pass metabolic processes which provide better bioavailability, rapid onset of action, and higher patient compliance. Dysphagia (difficulty in swallowing) is common among in all ages of people and more in pediatric, geriatric, and psychiatric patients. In terms of permeability, the sublingual area of oral cavity is more permeable than buccal area. Sublingual drug administration is applied in field of cardiovascular drugs, steroids, enzymes and barbiturates.

While there are various ondansetron formulations currently available, there is still a need in the art for a quick-onset sublingual spray formulation containing ondansetron, or a pharmaceutically acceptable salt thereof.

SUMMARY OF THE INVENTION

In one aspect, the present invention is directed to sublingual spray formulations comprising from about 1 to about 15% w/w ondansetron or a salt thereof and purified water.

In a further aspect, the present invention is directed to sublingual spray formulations comprising from about 1 to about 15% w/w ondansetron or a salt thereof, from about 10 to about 95% w/w purified water, and from about 2 to about 80% w/w cosolvent, wherein the % w/w is of the total formulation.

In another aspect, the present invention is directed to methods for treating or preventing nausea and emesis in humans associated with cancer therapies such as surgery, chemotherapy and/or radiation comprising administering the formulations of the present invention to a patient.

DETAILED DESCRIPTION

Applicants unexpectedly discovered a sublingual ondansetron formulation which has improved bioavailability, has a more rapid onset of action, has improved storage stability, and has excellent spray characteristics.

In one embodiment, the present invention is directed to sublingual spray formulations comprising from about 1 to about 15% w/w ondansetron or a salt thereof and purified water. Preferably, this formulation is propellant free.

Preferably, all of the formulations of the present invention are propellant free.

As used herein, "ondansetron" refers to the base or a pharmaceutically acceptable salt, ester, derivative, or prodrug thereof.

Pharmaceutically acceptable salts that can be used in accordance with the current invention include but are not limited to hydrochloride salts. In preferred embodiments the pharmaceutically acceptable salt is hydrochloride.

In another embodiment, the formulations of the present invention contain from about 10 to about 95% w/w purified water.

In a further embodiment, the formulations of the present invention contain a cosolvent selected from the group consisting of purified water, an alcohol, a glycol, and a mixture thereof. Preferably, the cosolvent is a mixture of an alcohol and a glycol.

In a preferred embodiment, from about 2 to about 80% w/w of the formulation is cosolvent. More preferably, from about 10 to about 60% w/w of the formulation is cosolvent.

In preferred embodiments, the formulations may contain from about from about 15 to about 60% w/w ethanol and/or from about 5 to about 25% w/w propylene glycol as cosolvents. In a more preferred embodiment, the formulations may contain about 31.5% w/w ethanol and about 15% w/w propylene glycol as cosolvents.

In some embodiments, the formulations of the present invention may also contain an effective amount of a pharmaceutically acceptable solubilizer. Suitable solubilizers include polysorbate, sorbitan, polyvinylpyrrolidine, sodium lauryl sulfate, cyclodextrin, or a mixture thereof. One presently preferred solubilizer is cyclodextrin.

When a solubilizer is used, the effective amount of the solubilizer is from about 0.01 to about 30% w/w of the formulation.

In another preferred embodiment, the formulations of the present invention contain a preservative. Preservatives include methyl paraben, ethyl paraben, butyl paraben, propyl paraben, sodium benzoate, benzoic acid, or a mixture thereof. Preferred preservatives are methyl paraben and propyl paraben.

When a preservative is used, the effective amount of the preservative is from about 0.01 to about 0.5% w/w of the formulation.

The formulations of the present invention may also contain a flavoring agent. Flavoring agents include menthol, fruit punch flavor, strawberry flavor, cherry flavor, raspberry flavor, mint flavor, orange oil, spearmint oil, citrus oil, peppermint oil, cinnamon oil, anise oil, or a mixture thereof. Preferred flavoring agents are menthol and fruit punch flavor.

When a flavoring agent is used, the effective amount of the flavoring agent is from about 0.01 to about 0.5% w/w of the formulation.

The formulations of the present invention may also contain a sweetener. Sweeteners include sucralose, sucrose, aspartame, neotame, saccharin, dextrose, mannitol, glycerin, xylitol, or a combination thereof. A preferred sweetener is sucralose.

When a sweetener is used, the effective amount of the sweetener is from about 0.01 to about 0.5% w/w of the formulation.

In a preferred embodiment, the sublingual spray formulations of the present invention are capable of producing a droplet size distribution wherein the mean Dv(10) is from about 10 to about 30 microns during administration.

In a preferred embodiment, the sublingual spray formulations of the present invention are capable of producing a droplet size distribution wherein the mean Dv(50) is from about 15 to about 80 microns during administration.

In yet another preferred embodiment, the sublingual spray formulations of the present invention are capable of producing a droplet size distribution wherein the mean Dv(90) is from about 40 to about 200 microns during administration.

In a further embodiment, the sublingual spray formulations of the present invention are capable of producing a spray plume that has an ovality ratio of from about 1.1 to 2.8.

In another preferred embodiment, the sublingual spray formulations of the present invention are capable of producing a spray plume width that is from about 15 to about 45 millimeters during administration.

In an embodiment of the present invention, the sublingual spray formulations comprise from about 1 to about 15% w/w ondansetron or a salt thereof, from about 10 to about 95% w/w purified water, and from about 2 to about 80% w/w cosolvent.

In another embodiment of the present invention, the sublingual spray formulations comprise from about 1 to about 15% w/w ondansetron or a salt thereof, from about 10 to about 95% w/w purified water, from about 2 to about 80% w/w cosolvent, from about 0.01 to about 0.5% w/w antimicrobial preservative, from about 0.01 to about 0.5% w/w sweetener, and from about 0.01 to about 0.5% w/w flavoring agent.

In a preferred embodiment, the sublingual spray formulations comprise from about 2 to about 10% w/w ondansetron or a salt thereof, from about 15 to about 70% w/w purified water, and from about 15 to about 60% w/w ethanol and from about 5 to about 25% w/w propylene glycol as cosolvents.

In a preferred embodiment, the sublingual spray formulations comprise from about 2 to about 10% w/w ondansetron or a salt thereof, from about 15 to about 70% w/w purified water, from about 15 to about 60% w/w ethanol, from about 5 to about 25% w/w propylene glycol as cosolvents, from about 0.01 to about 0.5% w/w antimicrobial preservative, from about 0.01 to about 0.5% w/w sweetener, and from about 0.01 to about 0.5% w/w flavoring agent.

In yet another preferred embodiment, the sublingual spray formulations of the present invention comprise about 3.93% w/w ondansetron hydrochloride dihydrate, about 48.73% w/w purified water, and about 31.5% w/w ethanol and about 15% w/w propylene glycol as cosolvents.

In yet another preferred embodiment, the sublingual spray formulations of the present invention comprise about 3.93% w/w ondansetron hydrochloride dehydrate, about 48.73% w/w purified water, about 31.5% ethanol and about 15% w/w propylene glycol as cosolvents, from about 0.01 to about 0.5% w/w antimicrobial preservative, from about 0.01 to about 0.5% w/w sweetener, and from about 0.01 to about 0.5% w/w flavoring agent.

In another embodiment, the present invention is directed to methods for treating or preventing nausea and emesis in humans associated with chemotherapy, radiation or surgery comprising administering the formulation of claim 1 to a patient in need thereof.

In a preferred embodiment, from about 50 to about 400 μL of the formulation of claim 1 is administered to a patient.

As used herein, "nausea" refers to the sensation of unease and discomfort in the upper stomach with an involuntary urge to vomit.

As used herein, "emesis" refers to the action of vomiting.

As used herein, "chemotherapy" refers to administering one or more cytotoxic anti-neoplastic drugs to a cancer patient as part of a standardized treatment regimen.

As used herein, "propellant free" refers to a sublingually administered formulation that is not administered using compressed gas.

As used herein the term "patient" refers, but is not limited to, a person that is being treated for nausea and emesis.

As used herein the term "pharmaceutically acceptable" refers to ingredients that are not biologically or otherwise undesirable in a sublingual dosage form.

As used herein the term "effective amount" refers to the amount necessary to treat a patient in need thereof.

As used herein "% w/w" and "percent w/w" refer to the percent weight of the total formulation.

As used herein, all numerical values relating to amounts, weights, and the like, that are defined as "about" each particular value is plus or minus 10%. For example, the phrase "about 10% w/w" is to be understood as "9% to 11% w/w." Therefore, amounts within 10% of the claimed value are encompassed by the scope of the claims.

The disclosed embodiments are simply exemplary embodiments of the inventive concepts disclosed herein and should not be considered as limiting, unless the claims expressly state otherwise.

The following examples are intended to illustrate the present invention and to teach one of ordinary skill in the art how to use the formulations of the invention. They are not intended to be limiting in any way.

EXAMPLES

Example 1

Preparation of Stable Ondansetron Sublingual Formulations

The excipients listed in Table 1 below were dissolved in either ethanol or purified water based on their solubility. Next, the solutions mixed together. Then, ondansetron was added to the final solution and mixed until it fully dissolved.

TABLE 1

Stable Sublingual Ondansetron Spray Formulations

| Formulation | 1 | 2 | 3 | 4 | 5 |
|---|---|---|---|---|---|
| Ondansetron Hydrochloride Dihydrate | 5.24 | 4.66 | 5.14 | 5.01 | 5.213 |
| Purified Water | 47.6 | 75.34 | 46.6 | 46.6 | 47.5 |
| Ethanol | 32.07 | | 38.17 | 28.3 | 31.247 |
| Propylene Glycol | 15 | | | 10 | 15 |
| Sodium sulfobutyl ether β-cyclodextrin | | 20 | 10 | 10 | |
| Methyl Paraben | 0.02 | | 0.02 | 0.02 | 0.02 |
| Propyl Paraben | 0.02 | | 0.02 | 0.02 | 0.02 |
| L-Menthol | 0.05 | | 0.05 | 0.05 | 0.05 |
| Sucralose | | | | | 0.8 |
| Fruit punch Flavor | | | | | 0.15 |

Values = % w/w

Example 2

Stability of the Ondansetron Sublingual Formulations of Example 1

Stability Data

Formulations 1 to 5 were subjected to stability test at 40° C.±2° C./75%±5% relative humidity ("RH") and 25° C.±2° C./60%±5% RH for six months. After two, three and six months samples were pulled and analyzed for stability. Assay and impurities were detected using high performance liquid chromatography with an ultraviolet detector. The assay was performed at 216 nm and indicated as a % of initial concentration. For all impurities, analysis was performed at 216 nm and expressed as a percent area. The stability data for Formulations 1 to 5 is summarized in Tables 2 to 11 below. "ND" means that the impurity was not detected and "BQL" means that the impurity was below a quantifiable limit. Relative retention time "RRT" is given for each impurity.

TABLE 2

Stability Data for Sublingual Ondansetron Spray Formulation 1 stored at 40° C. ± 2° C. under 75% ± 5% relative humidity.

| 40° C. | RRT | Formulation 1 | | | |
|---|---|---|---|---|---|
| | | 0 m | 2 m | 3 m | 6 m |
| Assay | | 100 | 100.02 | 101.1 | 100.46 |
| Impurity D | 0.28 | 0.02 | 0.03 | 0.04 | 0.06 |
| Unknown Impurity 1 | 0.78 | ND | ND | BQL | BQL |
| Unknown Impurity 2 | 0.86 | ND | ND | BQL | BQL |
| Total (% area) | | 0.02% | 0.03% | 0.04% | 0.06% |

TABLE 3

Stability Data for Sublingual Ondansetron Spray Formulation 2 stored at 40° C. ± 2° C. under 75% ± 5% relative humidity.

| 40° C. | RRT | Formulation 2 | | | |
|---|---|---|---|---|---|
| | | 0 m | 2 m | 3 m | 6 m |
| Assay | | 100 | 101.72 | 101.6 | 105.63 |
| Impurity D | 0.28 | 0.02 | 0.03 | 0.03 | 0.03 |
| Impurity F | 0.19 | ND | ND | ND | 0.16 |
| Unknown Impurity 1 | 0.78 | ND | ND | BQL | BQL |
| Unknown Impurity 2 | 0.86 | ND | ND | BQL | BQL |
| Total (% area) | | 0.02% | 0.03% | 0.03% | 0.19% |

TABLE 4

Stability Data for Sublingual Ondansetron Spray Formulation 3 stored at 40° C. ± 2° C. under 75% ± 5% relative humidity.

| 40° C. | RRT | Formulation 3 | | | |
|---|---|---|---|---|---|
| | | 0 m | 2 m | 3 m | 6 m |
| Assay | | 100 | 100.63 | 102.26 | 102.38 |
| Impurity D | 0.28 | 0.02 | 0.03 | 0.04 | 0.05 |
| Unknown Impurity 1 | 0.78 | ND | ND | BQL | BQL |
| Unknown Impurity 2 | 0.86 | ND | ND | BQL | BQL |
| Total (% area) | | 0.02% | 0.03% | 0.04% | 0.05% |

TABLE 5

Stability Data for Sublingual Ondansetron Spray Formulation 4 stored at 40° C. ± 2° C. under 75% ± 5% relative humidity.

| 40° C. | RRT | Formulation 4 | | | |
|---|---|---|---|---|---|
| | | 0 m | 2 m | 3 m | 6 m |
| Assay | | 100 | 100.22 | 100.97 | 101.1 |
| Impurity D | 0.28 | 0.02 | 0.03 | 0.04 | 0.05 |
| Unknown Impurity 1 | 0.78 | ND | ND | BQL | BQL |
| Unknown Impurity 2 | 0.86 | ND | ND | BQL | BQL |
| Total (% area) | | 0.02% | 0.03% | 0.04% | 0.05% |

TABLE 6

Stability Data for Sublingual Ondansetron Spray Formulation 5 stored at 40° C. ± 2° C. under 75% ± 5% relative humidity.

| 40° C. | RRT | Formulation 5 | | | |
|---|---|---|---|---|---|
| | | 0 m | 2 m | 3 m | 5 m |
| Assay | | 100 | 100.02 | 100.28 | 102.19 |
| Impurity D | 0.28 | 0.02 | 0.04 | 0.05 | 0.05 |
| Unknown Impurity 1 | 0.6 | ND | ND | ND | 0.07 |
| Total (% area) | | 0.02% | 0.04% | 0.05% | 0.12% |

TABLE 7

Stability Data for Sublingual Ondansetron Spray Formulation 1 stored at 25° C. ± 2° C. under 60% ± 5% relative humidity.

| 25° C. | RRT | Formulation 1 | | |
|---|---|---|---|---|
| | | 0 m | 3 m | 6 m |
| Assay | | 100 | 99.7 | 102.21 |
| Impurity D | 0.28 | 0.02 | 0.03 | 0.04 |
| Unknown Impurity 1 | 0.78 | ND | BQL | BQL |

TABLE 7-continued

Stability Data for Sublingual Ondansetron Spray Formulation 1 stored at 25° C. ± 2° C. under 60% ± 5% relative humidity.

| 25° C. | | Formulation 1 | | |
|---|---|---|---|---|
| | RRT | 0 m | 3 m | 6 m |
| Unknown Impurity 2 | 0.86 | ND | BQL | BQL |
| Total (% area) | | 0.02% | 0.03% | 0.04% |

TABLE 8

Stability Data for Sublingual Ondansetron Spray Formulation 2 stored at 25° C. ± 2° C. under 60% ± 5% relative humidity.

| 25° C. | | Formulation 2 | | |
|---|---|---|---|---|
| | RRT | 0 m | 3 m | 6 m |
| Assay | | 100 | 101.78 | 103.41 |
| Impurity D | 0.28 | 0.02 | 0.03 | 0.02 |
| Impurity F | 0.19 | ND | ND | 0.12 |
| Unknown Impurity 1 | 0.78 | ND | BQL | BQL |
| Unknown Impurity 2 | 0.83 | ND | BQL | BQL |
| Total (% area) | | 0.02% | 0.03% | 0.14% |

TABLE 9

Stability Data for Sublingual Ondansetron Spray Formulation 3 stored at 25° C. ± 2° C. under 60% ± 5% relative humidity.

| 25° C. | | Formulation 3 | | |
|---|---|---|---|---|
| | RRT | 0 m | 3 m | 6 m |
| Assay | | 100 | 100.89 | 101.8 |
| Impurity D | 0.28 | 0.02 | 0.03 | 0.03 |
| Impurity F | 0.19 | ND | ND | 0.05 |
| Unknown Impurity 1 | 0.78 | ND | BQL | BQL |
| Unknown Impurity 2 | 0.86 | ND | BQL | BQL |
| Total (% area) | | 0.02% | 0.03% | 0.08% |

TABLE 10

Stability Data for Sublingual Ondansetron Spray Formulation 4 stored at 25° C. ± 2° C. under 60% ± 5% relative humidity.

| 25° C. | | Formulation 4 | | |
|---|---|---|---|---|
| | RRT | 0 m | 3 m | 6 m |
| Assay | | 100 | 100.89 | 104.12 |
| Impurity D | 0.28 | 0.02 | 0.03 | 0.04 |
| Unknown Impurity 1 | 0.78 | ND | BQL | BQL |
| Unknown Impurity 2 | 0.86 | ND | BQL | BQL |
| Total (% area) | | 0.02% | 0.03% | 0.04% |

TABLE 11

Stability Data for Sublingual Ondansetron Spray Formulation 5 stored at 25° C. ± 2° C. under 60% ± 5% relative humidity.

| 25° C. | | Formulation 5 | | |
|---|---|---|---|---|
| | RRT | 0 m | 3 m | 5 m |
| Assay | | 100 | 98.13 | 100.54 |
| Impurity D | 0.28 | 0.02 | 0.04 | 0.03 |
| Unknown Impurity 1 | 0.78 | ND | BQL | BQL |

TABLE 11-continued

Stability Data for Sublingual Ondansetron Spray Formulation 5 stored at 25° C. ± 2° C. under 60% ± 5% relative humidity.

| 25° C. | | Formulation 5 | | |
|---|---|---|---|---|
| | RRT | 0 m | 3 m | 5 m |
| Unknown Impurity 2 | 0.86 | ND | BQL | BQL |
| Total (% area) | | 0.02% | 0.04% | 0.03% |

Formulations 1 to 5 all showed good stability at both temperature conditions, 40° C.±2° C./75%±5% RH and 25° C.±2° C./60%±5% RH, having total impurities less than 0.2% at six months. The concentrations of all of the excipients used in the formulations were based on the maximum allowable daily dosage recommendation by the US Food and Drug Administration ("FDA"), as indicated on the FDA's inactive ingredient list. The results from these stability studies show that all the excipients used in the formulations were compatible with ondansetron. These results represent sublingual spray formulations that would remain stable for two years at room temperature.

Example 3

Preparation of Another Stable Ondansetron Sublingual Formulation

Another Ondansetron Formulation was prepared using the same method as Example 1. The amount of ondansetron and the excipients are outlined below in Table 12.

TABLE 12

Another Sublingual Ondansetron Spray Formulation

| | Formulation 6 |
|---|---|
| Ondansetron Hydrochloride Dihydrate | 3.93 |
| Purified water | 48.73 |
| Ethanol | 31.5 |
| Propylene Glycol | 15 |
| Methyl Paraben | 0.02 |
| Propyl Paraben | 0.02 |
| L-Menthol | 0.05 |
| Sucralose | 0.6 |
| Fruit punch flavor | 0.15 |
| Total | 100 |

Values = % w/w

Example 4

Ondansetron Spray Droplet Size Distribution, Spray Pattern and Plume Geometry

Formulation 6 was used to evaluate spray characteristics of an ondansetron sublingual spray. Droplet analysis was conducted using standard laser analysis procedures known by those of skill in the art. Droplet size distribution ("DSD"), specifically $Dv_{10}$, $Dv_{50}$, $Dv_{90}$, and Span, were tested at two distances, 3 cm and 6 cm. $Dv_{10}$ refers to droplet size for which 10% of the total volume is obtained; $Dv_{50}$ refers to droplet size for which 50% of the total volume is obtained; $Dv_{90}$ refers to droplet size for which 90% of the total volume is obtained; Span refers to distribution span $(Dv_{90}-Dv_{10})/Dv_{50}$. Spray pattern ("SP"), specifically Dmin, Dmax, and ovality ratio were tested at two distances, 3 cm and 6 cm. Dmin refers to the shortest diameter of the spray pattern in mm, Dmax refers to the widest diameter of the spray pattern in mm, and ovality ratio refers to the ratio of Dmax to Dmin. The spay pattern is measured after impact onto an appropriate target upon activation of a spray pump. The ovality ratio is useful as it provides information regarding the shape and density of the spray pump plume. The droplet size distribution and spray pattern data are provided below in Tables 13 to 16.

TABLE 13

Droplet Size Distribution of Ondansetron Sublingual Spray Formulation 6 at 3 cm

| DSD 3 CM 25° C. | $Dv_{10}$ | $Dv_{50}$ | $Dv_{90}$ | Span |
|---|---|---|---|---|
| Mean | 10.4 µm | 26.9 µm | 69.6 µm | 2.2 |

TABLE 14

Droplet Size Distribution of Ondansetron Sublingual Spray Formulation at 6 cm

| DSD 6 CM 25° C. | Dv (10) | Dv (50) | Dv (90) | Span |
|---|---|---|---|---|
| Mean | 14.3 µm | 34.1 µm | 79.5 µm | 1.9 |

TABLE 15

Spray Pattern of Ondansetron Sublingual Spray Formulation at 3 cm

| SP 3 CM 25° C. | Dmin | Dmax | Ovality Ratio |
|---|---|---|---|
| Mean | 20.8 mm | 35.9 mm | 1.8 |

TABLE 16

Spray Pattern of Ondansetron Sublingual Spray Formulation at 6 cm

| SP 6 CM 25° C. | Dmin | Dmax | Ovality Ratio |
|---|---|---|---|
| Mean | 28.0 mm | 58.1 mm | 2.1 |

A challenge of creating an ondansetron sublingual spray formulation is that it must be capable of producing spray droplets that are over 10 microns in diameter. Spray droplets 10 microns or smaller could be inhaled into the lungs. The optimal particle size for sublingual spray droplets is from 20 to about 200 microns in diameter. It is desirable for the formulation to have droplet sizes near 20 because this increases the surface area and increased surface area exposure is one factor that contributes to a high bioavailability. Sublingual formulations should be able to maintain a consistent droplet size throughout its shelf life.

Formulation 6 yielded excellent droplet sizes and spray patterns for sublingual administration. The testing also revealed that the formulation dose remained consistent when administered with a spray pump.

We claim:
1. A sublingual spray formulation comprising:
   about 3.9 3% to about 5.2% w/w ondansetron or a salt thereof; about 46.6% to about 75.34% w/w purified water; and
   about 20.0% to about 48.3% w/w of an excipient selected from the group consisting of propylene glycol, ethanol, cyclodextrin, a binary combination thereof and a tertiary combination thereof,
   wherein the % w/w is of the total formulation.
2. The formulation of claim 1 wherein the formulation is propellant free.
3. The formulation of claim 1 further comprising an effective amount of a pharmaceutically acceptable preservative.
4. The formulation of claim 1 further comprising an effective amount of a pharmaceutically acceptable flavoring agent.
5. The formulation of claim 1 further comprising an effective amount of a pharmaceutically acceptable sweetener.
6. The formulation of claim 1 further comprising:
   about 0.01 to about 0.5% w/w antimicrobial preservative;
   about 0.01 to about 0.5% w/w sweetener; and
   about 0.01 to about 0.5% w/w flavoring agent.
7. The formulation of claim 1 comprising:
   about 3.93% w/w ondansetron hydrochloride dihydrate;
   about 48.73% w/w purified water;
   about 31.5% w/w ethanol; and
   about 15 w/w propylene glycol.
8. A method for treating nausea and emesis in humans associated with chemotherapy, radiation or surgery for cancer treatment comprising administering the formulation of claim 1 to a patient in need thereof.
9. The method of claim 8 wherein about 50 to about 400 µL of the formulation of claim 1 is administered to a patient.
10. The formulation of claim 1 comprising:
    about 5.24% w/w ondansetron hydrochloride dihydrate;
    about 47.6% w/w purified water;
    about 32.07% w/w ethanol; and
    about 15% w/w propylene glycol.
11. The formulation of claim 1 comprising:
    about 4.66% w/w ondansetron hydrochloride dihydrate;
    about 75.34% w/w purified water; and
    about 20% w/w cyclodextrin.
12. The formulation of claim 1 comprising:
    about 5.14% w/w ondansetron hydrochloride dihydrate;
    about 46.6% w/w purified water;
    about 38.17% w/w ethanol; and
    about 10% w/w cyclodextrin.
13. The formulation of claim 1 comprising:
    about 5.01% w/w ondansetron hydrochloride dihydrate;
    about 46.6% w/w purified water;
    about 28.3% w/w ethanol;
    about 10% w/w propylene glycol; and
    about 10% w/w cyclodextrin.
14. The formulation of claim 1 comprising:
    about 5.21% w/w ondansetron hydrochloride dihydrate;
    about 47.5 w/w purified water;
    about 31.25% w/w ethanol; and
    about 15% w/w propylene glycol.

* * * * *